US009622661B2

(12) United States Patent
Crisco, III et al.

(10) Patent No.: US 9,622,661 B2
(45) Date of Patent: *Apr. 18, 2017

(54) IMPACT MONITORING SYSTEM FOR PLAYERS ENGAGED IN A SPORTING ACTIVITY

(71) Applicant: Riddell, Inc., Rosemont, IL (US)

(72) Inventors: Joseph J. Crisco, III, Providence, RI (US); Richard M. Greenwald, Norwich, VT (US); Jeffrey J. Chu, Quechee, VT (US)

(73) Assignee: Riddell, Inc., Rosemont, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/047,176

(22) Filed: Oct. 7, 2013

(65) Prior Publication Data
US 2014/0039355 A1 Feb. 6, 2014

Related U.S. Application Data

(63) Continuation of application No. 10/997,832, filed on Nov. 24, 2004, now Pat. No. 8,554,509, which is a
(Continued)

(51) Int. Cl.
*A63B 71/10* (2006.01)
*A61B 5/11* (2006.01)
(Continued)

(52) U.S. Cl.
CPC ............ *A61B 5/0004* (2013.01); *A42B 3/046* (2013.01); *A61B 5/11* (2013.01); *A61B 5/4076* (2013.01);
(Continued)

(58) Field of Classification Search
CPC ............ A61B 2560/00; A61B 2560/02; A61B 2560/0204; A61B 2560/0209;
(Continued)

(56) References Cited

U.S. PATENT DOCUMENTS 3,646,606 A 2/1972 Buxton et al.
3,902,478 A 9/1975 Konopasek et al.
(Continued)

FOREIGN PATENT DOCUMENTS

DE 19707495 8/1998
EP 0315498 5/1989
(Continued)

OTHER PUBLICATIONS

Foxlin et al., Miniature 6-DOF Inertial System for tracking HMDs, Apr. 13-14, 1998, SPIE, Helmet and Head-Mounted Displays III, AeroSense 98, vol. 3362.
(Continued)

*Primary Examiner* — Adam J Eiseman
*Assistant Examiner* — Patrick Fernandes
(74) *Attorney, Agent, or Firm* — McDermott Will & Emery LLP

(57) ABSTRACT

The invention relates to a system and method for real-time impact monitoring of multiple players engaged in a sporting activity where each player wears a protective helmet. The system includes a sensing and control unit removably positioned in each helmet. The sensing and control unit has a sensor to detect helmet impact data, a processor to compare the detected impact data to profiles, and a transmitter to transmit impact data. The system also includes a remote unit for receiving the impact data transmitted from the helmets.

20 Claims, 5 Drawing Sheets

Related U.S. Application Data continuation of application No. 09/974,566, filed on Oct. 10, 2001, now Pat. No. 6,826,509.

(60) Provisional application No. 60/239,379, filed on Oct. 11, 2000.

(51) Int. Cl.
    *A61B 5/00* (2006.01)
    *A42B 3/04* (2006.01)
    *A63B 71/06* (2006.01)

(52) U.S. Cl.
    CPC .......... *A61B 5/6803* (2013.01); *A61B 5/6814* (2013.01); *A61B 5/7246* (2013.01); *A61B 5/742* (2013.01); *A61B 5/7475* (2013.01); *A63B 71/06* (2013.01); *A63B 71/10* (2013.01); *A63B 2208/12* (2013.01); *A63B 2230/60* (2013.01); *A63B 2243/007* (2013.01)

(58) Field of Classification Search
    CPC .... A61B 2560/0214; A61B 2560/0219; A61B 2560/0223; A61B 2560/0228; A61B 2560/0233; A61B 2560/0238; A61B 2560/0242; A61B 2560/0247; A61B 2560/0252; A61B 2560/0257; A61B 2560/0261; A61B 2560/0266; A61B 2560/0271; A61B 60/0276; A61B 60/256; A61B 5/11; A61B 5/6803; A61B 5/0004; A61B 5/7246
    USPC .......................... 600/595, 587, 300, 33, 511
    See application file for complete search history.

(56) References Cited

U.S. PATENT DOCUMENTS

| | | |
|---|---|---|
| 3,972,038 A | 7/1976 | Fletcher et al. |
| 3,972,320 A | 8/1976 | Kalman |
| 4,196,429 A | 4/1980 | Davis |
| 4,440,160 A | 4/1984 | Fischell et al. |
| 4,468,656 A | 8/1984 | Clifford et al. |
| 4,502,035 A * | 2/1985 | Obenauf ............ A63B 69/3608 340/323 R |
| 4,590,801 A | 5/1986 | Merhav |
| 4,608,998 A | 9/1986 | Murdock |
| 4,665,748 A | 5/1987 | Peters |
| 4,691,556 A | 9/1987 | Mellander et al. |
| 4,763,275 A | 8/1988 | Carlin |
| 4,763,284 A * | 8/1988 | Carlin ............................ 702/41 |
| 4,873,867 A | 10/1989 | McPherson et al. |
| 4,883,271 A * | 11/1989 | French ............... A63B 24/0021 273/454 |
| 4,982,452 A | 1/1991 | Chaise |
| 4,996,877 A | 3/1991 | Stewart |
| 5,221,088 A | 6/1993 | McTeigue et al. |
| 5,327,588 A | 7/1994 | Garneau |
| 5,331,969 A | 7/1994 | Silberstein |
| 5,348,008 A | 9/1994 | Bornn et al. |
| 5,383,363 A | 1/1995 | Kulmaczewski |
| 5,408,879 A | 4/1995 | Vreeburg et al. |
| 5,487,305 A | 1/1996 | Ristic et al. |
| 5,539,935 A | 7/1996 | Rush, III |
| 5,546,609 A * | 8/1996 | Rush, III ............ A41D 13/018 2/413 |
| 5,596,491 A | 1/1997 | Gold |
| 5,615,132 A | 3/1997 | Horton et al. |
| 5,621,922 A | 4/1997 | Rush, III |
| 5,645,077 A | 7/1997 | Foxlin |
| 5,697,099 A | 12/1997 | Siska, Jr. et al. |
| 5,704,707 A | 1/1998 | Gebelein et al. |
| 5,723,786 A | 3/1998 | Klapman |
| 5,745,028 A | 4/1998 | Hock |
| 5,819,206 A | 10/1998 | Horton et al. |
| 5,856,811 A | 1/1999 | Shih et al. |
| 5,896,590 A | 4/1999 | Fleisch |
| 5,916,181 A * | 6/1999 | Socci et al. ................... 600/595 |
| 5,978,972 A * | 11/1999 | Stewart .................. A42B 3/046 2/422 |
| 6,002,994 A | 12/1999 | Lane et al. |
| 6,009,563 A | 1/2000 | Swanson et al. |
| 6,032,530 A | 3/2000 | Hock |
| 6,056,674 A * | 5/2000 | Cook .................. A63B 71/0605 482/11 |
| 6,057,758 A | 5/2000 | Dempsey et al. |
| 6,090,044 A * | 7/2000 | Bishop ................. A61B 5/1071 128/920 |
| 6,186,145 B1 | 2/2001 | Brown |
| 6,198,394 B1 | 3/2001 | Jacobsen et al. |
| 6,259,944 B1 | 7/2001 | Margulis et al. |
| 6,298,483 B1 | 10/2001 | Schiebl et al. |
| 6,301,718 B1 | 10/2001 | Rigal |
| 6,302,844 B1 | 10/2001 | Walker et al. |
| 6,361,507 B1 | 3/2002 | Foxlin |
| 6,366,871 B1 | 4/2002 | Geva |
| 6,375,612 B1 | 4/2002 | Guichon et al. |
| 6,397,151 B1 | 5/2002 | Yamagishi et al. |
| 6,406,168 B1 | 6/2002 | Whiting |
| 6,441,747 B1 | 8/2002 | Khair et al. |
| 6,484,133 B1 | 11/2002 | Vogt |
| 6,539,336 B1 | 3/2003 | Vock et al. |
| 6,588,022 B1 | 7/2003 | Anders et al. |
| 6,611,782 B1 | 8/2003 | Wooster et al. |
| 6,611,789 B1 | 8/2003 | Darley |
| 6,647,787 B2 | 11/2003 | Fore |
| 6,730,047 B2 * | 5/2004 | Socci et al. ................... 600/595 |
| 6,735,551 B2 | 5/2004 | Voegeli et al. |
| 6,748,250 B1 | 6/2004 | Berman et al. |
| 6,826,509 B2 | 11/2004 | Crisco, III et al. |
| 7,054,784 B2 * | 5/2006 | Flentov et al. ............... 702/149 |
| 7,087,015 B1 | 8/2006 | Comrie et al. |
| 7,092,846 B2 | 8/2006 | Vock |
| 7,386,401 B2 * | 6/2008 | Vock et al. ..................... 702/44 |
| 7,526,389 B2 * | 4/2009 | Greenwald et al. ........... 702/55 |
| 7,693,668 B2 * | 4/2010 | Vock et al. ..................... 702/44 |
| 8,280,681 B2 * | 10/2012 | Vock et al. ................... 702/173 |
| 2002/0011250 A1 | 1/2002 | Stewart |
| 2002/0024450 A1 | 2/2002 | Townsend et al. |
| 2002/0060633 A1 | 5/2002 | Crisco et al. |
| 2002/0116147 A1 | 8/2002 | Vock et al. |
| 2002/0183657 A1 | 12/2002 | Socci et al. |
| 2003/0014210 A1 | 1/2003 | Vock et al. |
| 2003/0071766 A1 | 4/2003 | Hartwell et al. |
| 2003/0151554 A1 | 8/2003 | McCarthy |
| 2003/0163287 A1 | 8/2003 | Vock et al. |
| 2003/0217582 A1 | 11/2003 | Reinbold et al. |
| 2004/0008106 A1 | 1/2004 | Konczal |
| 2004/0225236 A1 * | 11/2004 | Wheeler et al. .............. 600/595 |
| 2004/0240198 A1 | 12/2004 | Van Laar et al. |
| 2005/0177929 A1 | 8/2005 | Greenwald et al. |
| 2006/0038694 A1 | 2/2006 | Naunheim et al. |
| 2006/0074338 A1 | 4/2006 | Greenwald et al. |
| 2007/0061106 A1 * | 3/2007 | Vock et al. ................... 702/182 |
| 2010/0076692 A1 * | 3/2010 | Vock et al. ..................... 702/19 |
| 2011/0215931 A1 * | 9/2011 | Callsen et al. ............. 340/573.1 |

FOREIGN PATENT DOCUMENTS

| | | |
|---|---|---|
| WO | 9836213 | 8/1998 |
| WO | 9904685 | 2/1999 |
| WO | WO-9904685 | 2/1999 |
| WO | 02053024 | 7/2002 |
| WO | WO-02053024 | 7/2002 |
| WO | 2006036567 | 4/2006 |
| WO | WO-2006036567 | 4/2006 |

OTHER PUBLICATIONS

Padgaonkar, A.J., Krieger, K.W.; King, A.I.; "Measurement of Angular Acceleration of a Rigid Body Using Linear Accelerometers", Journal of Applied Mechanics, Sep. 1975 pp. 552-556.

(56) References Cited

OTHER PUBLICATIONS

Puers et al., A Telemetry System for the Detection of Hip Prosthesis Loosening by Vibration Analysis, Aug. 25, 2000, Sensors and Actuators, vol. 85, pp. 42-47.

Bai et al., A Portable ECG and Blood Pressure Telemonitoring System, Jul./Aug. 1999, IEEE Engineering in Medicine and Biology, pp. 63-70.

Naunheim et al., Comparison of Impact Data in Hockey, Football, and Soccer. Journal of Trauma and Acute Care Surgery 48.5, 2000, pp. 938-941.

Moon, Donald W.; Beedle Charles W.; and Kovacic, Charles R.; "Peak Head Acceleration of Football", Medicine and Science in Sports, vol. 3 No. 1 pp. 44-50, Spring 1971.

Coleman et al., Ambient Head Temperature and Football Helmet Design, Mar. 1972, Medicine, Science, Exercise and Sports Journal, 19 pages.

Reid, Stephen E. M.D.; Epstein, Herbert M. M.D.; O'Dea, Thomas J. MA; Louis, Michael W. and Reid, Stephen E, Jr.; "Head Protection in Football", Sports Medicine, Mar./Apr. 1974 pp. 86-92.

Padgaonkar, A.J., Krieger, K.W.; King, A.I.;. "Measurement of Angular Acceleration of a Rigid Body Using Linear Accelerometers", Journal of Applied Mechanics, Sep. 1975 pp. 552-556.

Merono et al., Movement Evaluator System Via R.F. Transmission, 1995 IEEE, pp. 94-97.

Foxlin et al., Miniature 6-DOF Inertial System for tracking HMDs, Apr. 13-14 1998, SPIE, Helmet and Head-Mounted Displays III, AeroSense 98, vol. 3362.

Medendorp et al., Off-centric Rotation Axes in Natural Head Movements: Implications for Vestibular Reafference and Kinematic Redundancy, 1998, The American Physiological Society, pp. 2025-2039.

Bai et al., A Portable ECG and Blood Pressure Telemonitorng Syem Jul./Aug. 1999 IEEE Engineeringin Medicine and Biology. pp. 63-70.

King, A. I. et al. "Mechanics of the Head/Neck." The Biomedical Engineering Handbook: Second Edition. Dec. 28, 1999. CRC Press LLC. pp. 23-1:23-12.

Puers et al., A Telemetry System for the Detection of Hip Prosthesis Loosening by Vibration Analysis, Aug. 25, 2000, Sensors and Actuators; vol. 85, pp. 42-47.

Gibilisco, Stan, ed. "Encode." The Illustrated Dictionary of Electronics. McGraw-Hill. 2001. Eighth edition. p. 257.

Schatz et al., Computer-Based Assessment of Sports-Related Concussion, 2003, Applied Neuropsychology, vol. 10, No. 1, pp. 42-47.

Murray, C., Smart Helmets Monitor Football Injuries, Dec. 18, 2003, Embedded.com.

International Search Report for PCT/US2005/032903 mailed Mar. 10, 2006.

International Search Report for PCT/US2006/000536 mailed Oct. 2, 2006.

Written Opinion for PCT/US2006/000536 mailed Jul. 10, 2007.

* cited by examiner

IMPACT MONITORING SYSTEM FOR PLAYERS ENGAGED IN A SPORTING ACTIVITY

CROSS-REFERENCE TO RELATED APPLICATIONS

This application is a continuation of U.S. patent application Ser. No. 10/997,832, filed Nov. 24, 2004, which is a continuation of U.S. patent application Ser. No. 09/974,566, filed Oct. 10, 2001, now U.S. Pat. No. 6,826,509, which claims the benefit of Provisional Application Ser. No. 60/239,379, filed Oct. 11, 2000.

FEDERALLY SPONSORED RESEARCH OR DEVELOPMENT

The invention described herein was made in the course of work under grant number 1R43HD4074301 from the National Institutes of Health. The U.S. Government may retain certain rights in this invention.

BACKGROUND OF THE INVENTION

The present invention relates to recording of the magnitude and direction of impact to and the linear and rotational acceleration of a body part, such as a human head, of person engaged in physical activity, such as during the play of a sport.

More particularly, it relates to a helmet based system which is typically worn while playing a sport such as football or hockey, and to the method of recording and storing data relating to the linear and rotational accelerations of the person's body part due to impact forces acting thereon. The present invention relates also to head mounted systems which are also worn during game play, such as a head band, that does not employ helmets, such as soccer.

It should be understood that the present invention relates generally to the linear and rotational acceleration of a body part, and most importantly, the head. The present invention, as will be discussed in detail below, is capable of monitoring any body part of an individual but has particular application in monitoring the human head. Therefore, any reference to a body part is understood to encompass the head and any reference to the head alone is intended to include applicability to any body part. For ease of discussion and illustration, discussion of the prior art and the present invention is directed to the head of human, by way of example and is not intended to limit the scope of discussion to the human head.

There is a concern in various contact sports, such as football and hockey, of brain injury due to impact to the head. During such physical activity, the head or other body part of the individual, is often subjected to direct contact to the head which results in impact to the skull and brain of the individual as well as movement of the head or body part itself.

Much remains unknown about the response of the brain to head accelerations in the linear and rotational directions and even less about the correspondence between specific impact forces and injury, particularly with respect to injuries caused by repeated exposure to impact forces of a lower level than those that result in a catastrophic injury or fatality. Almost all of what is known is derived from animal studies, studies of cadavers under specific directional and predictable forces (i.e. a head-on collision test), from crash a dummies, from human volunteers in well-defined but limited impact exposures or from other simplistic mechanical models. The conventional application of known forces and/or measurement of forces applied to animals, cadavers, crash dummies, and human volunteers limit our knowledge of a relationship between forces applied to a living human head and resultant severe and catastrophic brain injury. These prior studies have limited value as they typically relate to research in the automobile safety area.

The concern for sports-related injuries, particularly to the head, is higher than ever. The Center for Disease Control and Prevention estimates that the incidence of sports-related mild traumatic brain injury (MTBI) approaches 300,000 annually in the United States. Approximately ⅓ of these injuries occur in football. MTBI is a major source of lost player time. Head injuries accounted for 13.3% of all football injuries to boys and 4.4% of all soccer injuries to both boys and girls in a large study of high school sports injuries. Approximately 62,800 MTBI cases occur annually among high school varsity athletes, with football accounting for about 63% of cases. Concussions in hockey affect 10% of the athletes and make up 12%-14% of all injuries.

For example, a typical range of 4-6 concussions per year in a football team of 90 players (7%), and 6 per year from a hockey team with 28 players (21%) is not uncommon. In rugby, concussion can affect as many as 40% of players on a team each year. Concussions, particularly when repeated multiple times, significantly threaten the long-term health of the athlete. The health care costs associated with MTBI in sports are estimated to be in the hundreds of millions annually. The National Center for Injury Prevention and Control considers sports-related traumatic brain injury (mild and severe) an important public health problem because of the high incidence of these injuries, the relative youth of those being injured with possible long term disability, and the danger of cumulative effects from repeat incidences.

Athletes who suffer head impacts during a practice or game situation often find it difficult to assess the severity of the blow. Physicians, trainers, and coaches utilize standard neurological examinations and cognitive questioning to determine the relative severity of the impact and its effect on the athlete. Return to play decisions can be strongly influenced by parents and coaches who want a star player back on the field. Subsequent impacts following an initial concussion (MTBI) may be 4-6 times more likely to result in a second, often more severe, brain injury. Significant advances in the diagnosis, categorization, and post-injury management of concussions have led to the development of the Standardized Assessment of Concussion (SAC), which includes guidelines for on-field assessment and return to sport criteria. Yet there are no objective biomechanical measures directly related to the impact used for diagnostic purposes. Critical clinical decisions are often made on the field immediately following the impact event, including whether an athlete can continue playing. Data from the actual event would provide additional objective data to augment psychometric measures currently used by the on-site medical practitioner.

Brain injury following impact occurs at the tissue and cellular level, and is both complex and not fully understood. Increased brain tissue strain, pressure waves, and pressure gradients within the skull have been linked with specific brain injury mechanisms. Linear and rotational head acceleration are input conditions during an impact. Both direct and inertial (i.e. whiplash) loading of the head result in linear and rotational head acceleration. Head acceleration induces strain patterns in brain tissue, which may cause injury. There is significant controversy regarding what biomechanical information is required to predict the likelihood and severity of MTBI. Direct measurement of brain dynamics during impact is extremely difficult in humans.

Head acceleration, on the other hand, can be more readily measured; its relationship to severe brain injury has been postulated and tested for more than 50 years. Both linear and rotational acceleration of the head play an important role in producing diffuse injuries to the brain. The relative contributions of these accelerations to specific injury mechanisms have not been conclusively established. The numerous mechanisms theorized to result in brain injury have been evaluated in cadaveric and animal models, surrogate models, and computer models. Prospective clinical studies combining head impact biomechanics and clinical outcomes have been strongly urged. Validation of the various hypotheses and models linking tissue and cellular level parameters with MTBI in sports requires field data that directly correlates specific kinematic inputs with post-impact trauma in humans.

In the prior art, conventional devices have employed testing approaches which do not relate to devices which can be worn by living human beings, such as the use of dummies. When studying impact with dummies, they are typically secured to sleds with a known acceleration and impact velocity. The dummy head then impacts with a target, and the accelerations experienced by the head are recorded. Impact studies using cadavers are performed for determining the impact forces and pressures which cause skull fractures and catastrophic brain injury.

There is a critical lack of information about what motions and impact forces lead to MTBI in sports. Previous research on football helmet impacts in actual game situations yielded helmet impact magnitudes as high as 530 g's for a duration of 60 msec and >1000 g's for unknown durations with no known MTBI. Accelerometers were held firmly to the head via the suspension mechanism in the helmet and with Velcro straps. A recent study found maximum helmet accelerations of 120 g's and 150 g's in a football player and hockey player, respectively. The disparity in maximum values among these limited data sets demonstrates the need for additional large-scale data collection.

Most prior art attempts relate to testing in a lab environment. However, the playing field is a more appropriate testing environment for accumulating data regarding impact to the head. A limitation of the prior art involves practical application and widespread use of measurement technologies that are size and cost effective for individuals and teams. Therefore, there would be significant advantage to outfitting an entire playing team with a recording system to monitoring impact activities. This would assist in accumulating data of all impacts to the head, independent of severity level, to study the overall profile of head impacts for a given sport. Also, full-time head acceleration monitoring would also be of great assistance in understanding a particular impact or sequence of impacts to a player's head over time that may have caused an injury and to better treat that injury medically.

To address this need, there have been many attempts in the prior art to provide a system for recording the acceleration of an individual's body part, such as their head. For example, prior art systems have employed tri-axial accelerometers which are affixed as a module to the back of a football helmet. Such tri-axial accelerometers provide acceleration sensing in the X, Y and Z directions which are orthogonal to each other. Tri-axial accelerometer systems require that the accelerometers be orthogonal to each other Also, such tri-axial accelerometer systems have been extremely expensive making it cost prohibitive for widespread commercial installation on an entire team.

Prior art systems, have also attempted to precisely locate the various combinations of linear and rotational accelerometers, in specific orthogonal arrays, within a helmet to obtain complete three-dimensional head kinematics. Such arrays require that the accelerometers be positioned orthogonal to each other. It is impractical, from a size, cost and complexity standpoint, for commercial application of such arrays in helmet or head mounted systems.

Obviously, accelerometer arrays for measuring linear and rotational accelerations cannot be readily mounted inside the human head, as is done with instrumented test dummy heads. Other sensing technologies, such as gyroscopes, magnetohydrodynamic angular rate sensors and GPS sensors, do not currently fulfill the practical and technical specifications for a commercially available system. Also, the use of multi-axis accelerometer systems placed in a mouthguard are impractical because wires need to run from the helmet or backpack into the user's mouth from the power source and to a telemetry unit, which might present a hazard to the players and limited compliance among them.

In view of the foregoing, there is a demand for a head acceleration sensing system that can be manufactured and installed at very low cost to permit widespread utilization. There is a demand for a system that can be installed in many, many individuals, such as an entire football team roster of over 60 players, to provide research opportunities and data that have not yet been available to the scientific community before. Further, there is a demand for a system and method for measuring the linear and rotational acceleration of a body part that is easy to install and comfortable for the individual to wear. There is also a desire to provide a low-cost system and method that can record and accurately estimate linear and rotational acceleration of a body part.

The present invention is provided to solve the problems discussed above and other problems, and to provide advantages and aspects not provided by prior * of this type. A full discussion of the features and advantages of the present invention is deferred to the following detailed description, which proceeds with reference to the accompanying drawings.

SUMMARY OF THE INVENTION

The present invention preserves the advantages of prior art body part acceleration systems and associated methods. In addition, it provides new advantages not found in currently available methods and systems and overcomes many disadvantages of such currently available methods and systems.

The invention is generally directed to the novel and unique head acceleration monitoring technology that is a highly portable system that designed to measure and record acceleration data in linear directions and to estimate rotational accelerations of an individual's head and direction and magnitude of impact during normal activity, such as during game play. While the present invention is specifically developed for the head, monitoring of other body parts, or the body in general, is envisioned and considered within the scope of the present invention.

The system and method of the present invention offers the opportunity to study head acceleration, human tolerance limits, the range and direction of accelerations in humans in relation to morphological features (e.g., neck circumference, head volume, neck length), and the relationship between precise measures of head acceleration in linear and rotational directions and acute consequence to brain physiology and function. Moreover, it provides the ability to measure an individual's cumulative exposure to linear and rotational accelerations while allowing unaffected performance of everyday sports and activities.

The system and method of the present invention is designed as a standard component of otherwise conventional sporting gear, in particular the helmet or as an independent head mounted system. The system and method of the present invention is designed for determining the magnitude of linear acceleration and direction of impact to a body part as well as the rotational acceleration of a body part, such as a head. A number, such as three, single-axis accelerometers are positioned proximal to the outer surface of the body part and about a circumference of the body part in a known spaced apart relation from one another. The accelerometers are oriented to sense respective linear acceleration orthogonal to the outer circumference of the body part. Dual-axis or tri-axis accelerometers may also be employed to provide an additional direction of acceleration sensing which is tangential to the surface of the skull of the head. Such tangential acceleration data may be optionally employed in further analysis.

The acceleration data sensed is recorded for each accelerometer. A hit profile function is determined from the configuration (i.e. geometry) of the body part and the positioning of the plurality of accelerometers thereabout. A number of potential hit results are generated from the hit profile function and then compared to the acceleration data sensed by the accelerometers. One of the potential hit results is best fit matched to the acceleration data to determine a best fit hit result. The magnitude acceleration and direction of acceleration due to an impact to the body part are determined from applying the hit profile function to the best fit hit result. The rotational acceleration of the body part can also be estimated from the magnitude and direction of the impact to the body part.

The data recorded is either recorded on a memory card or other mass memory means installed locally in the helmet, or is transmitted to a nearby receiver for storage on a computer's hard drive or other conventional mass storage device using conventional telemetry technology. The present invention provides storage of data over a length of time such that cumulative exposure effects and thus limits can be established for further or future participation in the sport by the individual wearing the helmet equipped with the present invention. The data also allows detection of impacts to the head which precede the occurrence of a brain injury. For this purpose the system and method of the present invention could be modified to record detailed data only when the accelerations exceed a defined threshold. The data may be processed immediately as the data is recorded, or at a later time so as to integrate and otherwise determine the linear, rotational and normal components of acceleration of the player's head.

The present invention is applicable for use with other parts of the body. For instance, other applications could include the study of the acceleration of body parts in relation to each other (e.g., among pole vaulters, high jumpers, or gymnasts), or to understand factors affecting acceleration in sprinters and swimmers (e.g., starting and turns).

Because of its portability, small size, and convenient light weight, the system and associated method of the present invention can also be used to study the acceleration of the body parts of live animals. For example, the acceleration and deceleration of birds in flight could be studied with a modified version of the present invention.

It is therefore an object of the present invention to employ accelerometers arranged in a manner orthogonal to the surface of the body part instead of arrays of accelerometers orthogonal to each other.

It is a further object of the invention to provide an inexpensive system that can still achieve results which are within the acceptable range of error for the given scientific question, study or hypothesis.

Another object of the present invention is to provide a system and method of calculating and estimating the linear and rotational acceleration that is easy to install and is comfortable for the individual to wear without affecting their game play either in a helmet or head band environment.

It is yet another object of the present invention to provide a system and method of measuring and calculating the linear and rotational acceleration that can be installed commercially at low cost. Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which.

DETAILED DESCRIPTION

Figure 1:
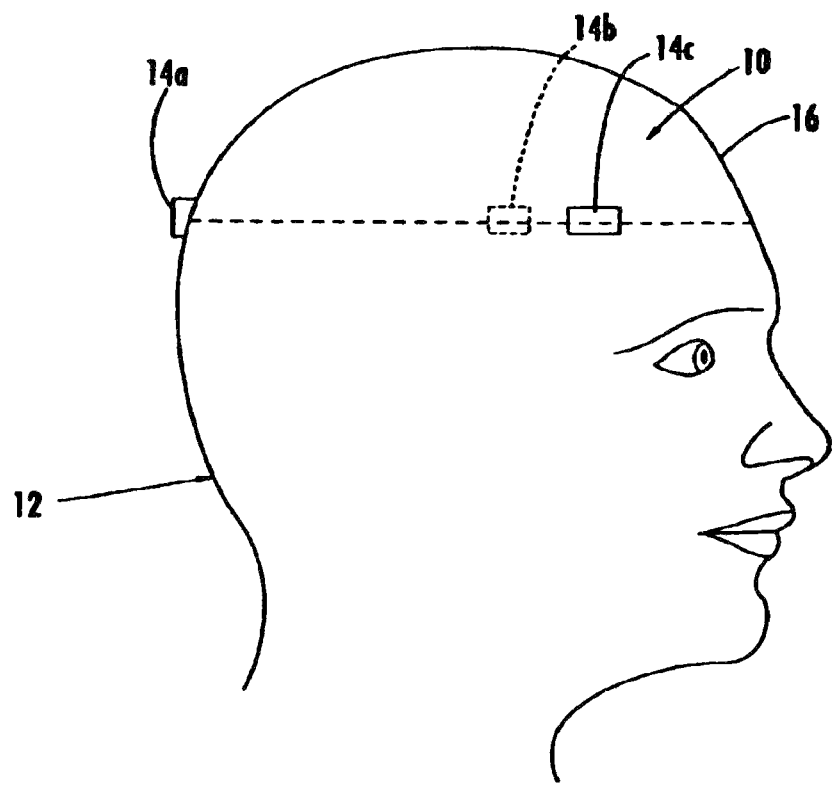
FIG. 1 is a side view the system of the present invention installed in a football helmet on an individual's head.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention provides a system and method for measuring, i.e. estimating, the linear and rotational acceleration of a body part. For ease of illustration, the body part will be described below as a human head. Unlike the prior art, the present invention uses single axis accelerometers orthogonal to the surface of the body part and not necessarily orthogonal to each other to enable the estimation of both the linear acceleration and rotational acceleration of the body part.

Figure 2:
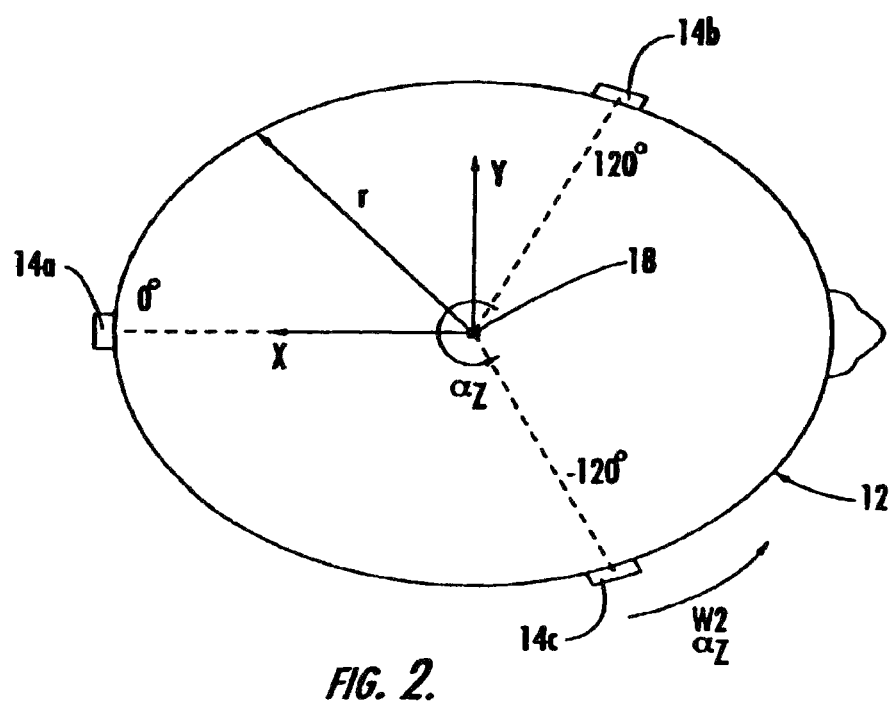
FIG. 2 is a top view of the system shown in FIG. 1.

Referring first to FIG. 1, a side view of an installed system 10 of the preferred embodiment of the present invention installed on body part 12, namely a human head. FIG. 2 shows a top view of this system 10 of the preferred embodiment of the present invention. The system 10 includes an array of accelerometers, generally referenced as 14, positioned about the periphery of the skull 16 of the head 12. Preferably, an array of 3 accelerometers 14 or more are located as close as possible to the outer surface of the skull 16 and arranged in the same plane which preferably passes through the center of gravity 18 of the body part 12. However, less than three accelerometers 14 may be used and the arrangement of the accelerometers 14 may be in different configurations around the surface of the skull, provided that their sensitive axis is orthogonal to the surface of the skull. The array of accelerometers defines a band about the skull 16 of the head 12.

In the preferred embodiment shown in FIGS. 1 and 2, an array of three accelerometers 14a, 14b and 14c are provided and are positioned at known positions about the outer periphery of the skull 16. As shown in FIG. 2 and in accordance with the coordinate system defined in FIG. 3, accelerometer 14a is positioned at 0 degrees while accelerometer 14b is positioned at 120 degrees and accelerometer 14c at −120 degrees. The use of as few accelerometers 14 as possible to estimate linear and rotational acceleration of the head 12 within a prescribed error tolerance is balanced against the cost associated of the system, namely the added cost per accelerometer 14 and associated circuitry 15 employed. If greater accuracy of the estimation of the linear and rotational acceleration of the head 16 is desired, the number of accelerometers 14 may be increased to improve the overall "goodness of fit" of the actual acceleration measurements to the estimation of linear and rotational acceleration of the head 16.

Figure 4:
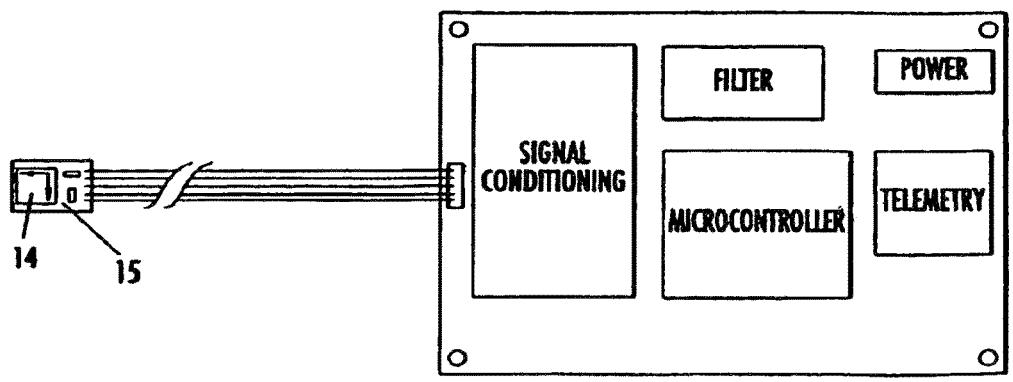
FIG. 4 is a perspective view of an accelerometer employed in the present invention.

The Analog Devices ADXL193/278 family of accelerometers are preferred for use in the system 10 of the present invention. An example of the a preferred accelerometer 14 is shown in FIG. 4. The ADXL278 is similar to the ADXL 193 except that it is a two-axis accelerometer rather than single-axis. Critical specifications include: small size (4.5 mm×4.5 mm×2.0 mm), low mass (1.5 g), operation at 3.3 V, high output (250 g max), high sensitivity (27 mv/g) and low cost. One axis measures accelerations towards the center of the head, while the second axis measures acceleration tangential to the surface of the head. While a single-axis accelerometer 14 is preferred, the second axis measurement of the ADXL 278 can also provide additional acceleration information for further processing and analysis. This second axis includes additional data tangential to the head during rotational experiments in the laboratory. While the ADXL 193/278 family of accelerometers are preferred, other accelerometers 14 may be employed to carry out the present invention.

In accordance with the present invention, the accelerometers 14 must be held close to the skull 16 of the head 12 to best measure the acceleration of the head. Direct attachment of accelerometers to the head is optimal but not feasible. Attempts to mount accelerometers directly to the helmet shell result in measures of helmet deformation rather than head acceleration. Variations among football helmet padding and liners and other helmet designs for other sports demand generic mounting concepts that are universally applicable. Thus, the mounting of the accelerometers 14 should not alter helmet performance or protrude from existing internal padding more than 1 mm. Also, the accelerometers 14 should be contained within and/or attached to the helmet to allow easy removal of both the helmet or headband and the accelerometers 14.

Figure 5:
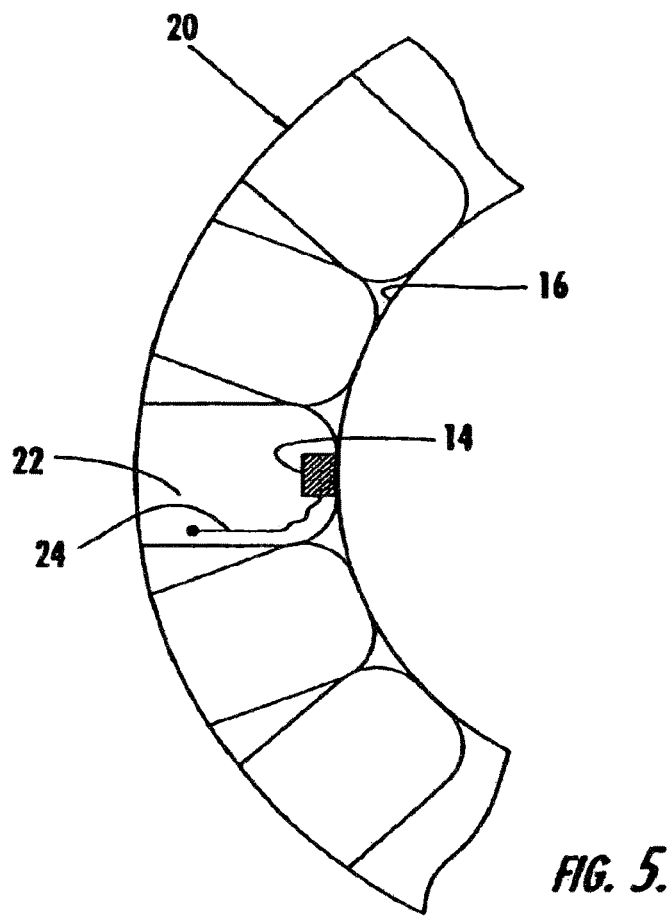
FIG. 5 is a side elevational view of a accelerometer embedded within cushioning of a football helmet.

The present invention provides a structure for maintaining the accelerometers 14 in a position as close as possible to the skull 16 while being as comfortable as possible. As shown in FIG. 5, it has been discovered that the preferred structure for positioning of the accelerometers proximate to the skull is to contain the accelerometers 14 within an air bladder 22 mounted within the helmet, generally referenced as 20.

As shown in FIG. 5, the preferred embodiment for carrying the accelerometers is to capture the accelerometer 14 inside an air-bladder 22 itself such that the pressure inside the bladder 22 will provide the force necessary to place the accelerometer 14 in direct apposition to the skull 16 of the head 12 when the bladder 22 is inflated. Additional accelerometers 14 are respectively placed in appropriately positioned air bladders 22 within the helmet 20 to provided the array of accelerometers as described above. In accordance with this attachment method, an RF welding process can be employed to pass the requisite cabling 24 through the bladder seal without compromising the integrity of the bladder 22. A significant advantage of this method is that, for a given padding configuration, the accelerometers 14 will be oriented similarly for all players using that model helmet 20.

Figure 6:
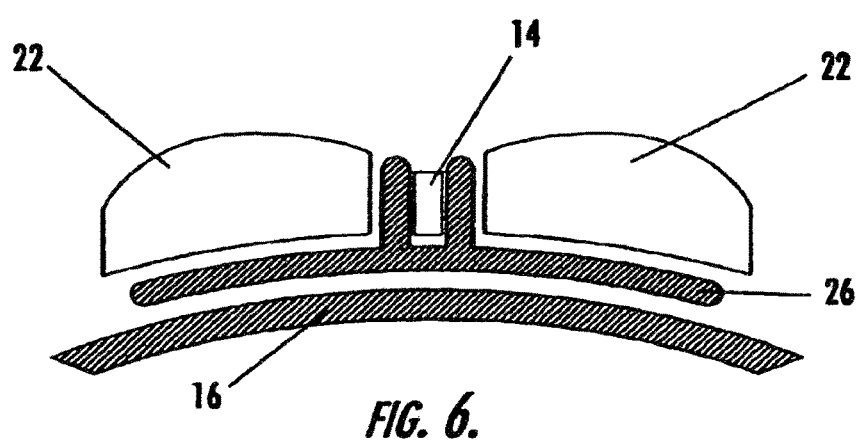
FIG. 6 is a side elevational view of an accelerometer held in place in a helmet by a T-shaped holder.

Alternatively, as shown in FIG. 6, the accelerometers 14 may be respectively installed in a plastic T-shaped holder 26 for placing the accelerometers 14 approximately in apposition to the skull 16 of the head 12. Each plastic T-shaped holder 26 respectively holds an accelerometer 14 between the cushions 22 in a football helmet and in direct apposition to the surface of the skull 16. This T-shaped accelerometer holder 26, for example, may be constructed of Delrin and with a 4 mm slot 28 for holding and orienting the accelerometer 14. The T-shaped holder 26 is pressed against the skull 16 of the head 12 when the air bladders 22 are inflated to 20 psi, for example. This structure for positioning the accelerometers 14 may not be preferred because it is possible that the users could feel the accelerometers 14 pushing against the skull 16 of their head 12.

Also, direct attachment of the accelerometers 14 to the air bladder 22 of the helmet 20 with a foam covering (not shown) is possible, although not preferred, because the sensitive axis of these devices is along a plane parallel to the top of the device. The minimum dimension of the accelerometer 14 and its mounting board 15, as shown in FIG. 4, in that direction is 7 mm, which caused the unit to act effectively as a point source against the head 12.

Still further and within the scope of the present invention, a mesh net or bandana carrying the array of accelerometers 14 units may be worn on the head or coupled to the inside of the helmet or a multi-layer soft foam interface that captured the accelerometers between layers or a spring-loaded construct attached to the shell of the helmet 20 between the foam pads (not shown) and air bladders 22.

Figure 7:
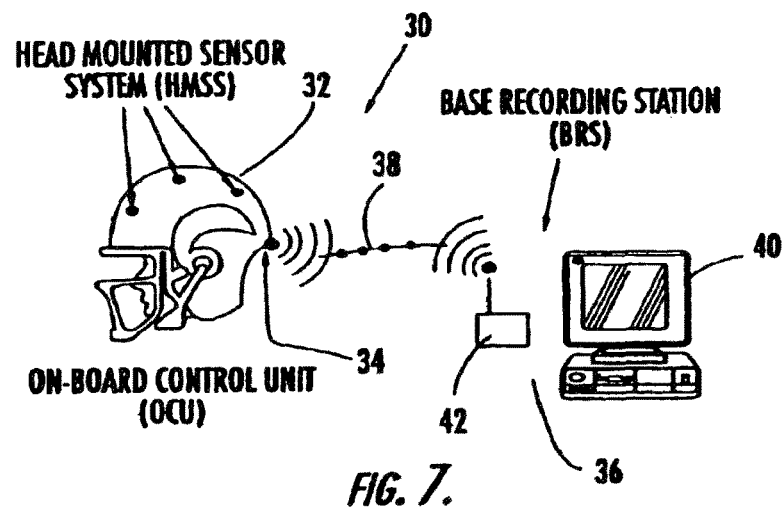
FIG. 7 is a diagram illustrating the wireless telemetry system optionally employed in the present invention.

As shown in FIG. 7, the above described array of accelerometers 14 are electrically interconnected together to form an entire system 30 for the collection, recording and processing of head acceleration data. The system includes the accelerometers 14 in an array in a head-mounted sensor system (HMSS), generally referred to as 32, an on-board control unit (OCU), generally referred to as 34, and a base recording station (BRS), generally referred to as 36. Preferably, the data connection 38 between the OCU 34 and BRS 36 is preferably wireless, however, a hardwired, tethered connected 38 is also possible. Together, these components provide a telemetered data acquisition system 30 for monitoring and recording sensor data on head impacts. The installed environment for the system 32 need not always be a helmet, and can be adapted for use in various forms in helmets or headgear for sports including football, hockey, soccer, lacrosse, wrestling, boxing and others. The HMSS unit 32 can be comprised of various additional sensors including displacement, load, pressure, acceleration, temperature, etc. In the current configuration, the HMSS 32 system is composed of multiple accelerometers 14 as described in detail above.

In FIG. 7, the BRS 36 and OCU 34 are preferably specified to be active during all practice and game situations. For team or multiple user configurations, the BRS 36 is either a laptop or PC 40, which is serially linked to a receiver 42 with capability for simultaneous transmission from up to 100 OCU transmitters 34. Calculations show that at a data transfer rate of 19.2 kbps, with maximum 100 bytes of information from each OCU 34 per impact, data from all 22 players on the field at any one time in sports such as soccer or football could be downloaded to the BRS 36 within 1 second. For single user configurations, the BRS 36 could be a stand-alone data-logger, or could be contained internally within the OCU 34, with plug in capability for downloading of data and programming. Triggering conditions programmed into the OCU 34 activate the transmitter/data collection system 30 and send information to the BRS 36. Power is conserved by turning the transmitter portion of the OCU 34 on only when an impact event occurs. For example, a minimum acceleration of 10 g's might be set as the trigger. Each OCU 34 uniquely identifies a given helmet 20 in the field and encodes the information so that the BRS 36 can properly multiplex and decode information from multiple OCU's.

In accordance with the present invention, a miniature telemetry system 30 is provided with a transmitter/receiver that preferably operates in the 900 MHz range with a range of at least 150 m. Analog signals from the accelerometers 14 will be time-division multiplexed (TDM) for transmission to the BRS. The size of the OCU 34 is specified to be no larger than 5 cm long×2.5 cm high×2.5 cm wide, or the size of 2 small AA batteries. The OCU 34 can be mounted at the base of the helmet 20 in the rear just above the neckline without interfering with player motion and without creating an injury hazard. The OCU 34 must contain the battery, the transmitter, and signal conditioning for the accelerometers.

The preferred accelerometers 14 operate at 3.3 V, the amplifier boards 15 power the accelerometers 14 and provide signal conditioning for the raw accelerometer signals with a 10 Hz high pass filter to eliminate static measurements (such as player shaking his head). The chips of the ADXL93/278 accelerometers have a 400 Hz 2-pole Bessel filter on-board. An additional 3000 Hz low pass filter on the amplifier board reduced high frequency noise that might enter the circuit after the accelerometer chip 15 and before the amplifier.

Details of the above system 30 set forth a preferred construction for carrying out the present invention. Such a system 30 may be modified to suit the needs of the particular application at hand, namely the environment of installation, required capacity, durability and cost. Such modified systems 30 are deemed to be within the scope of the present invention.

Acceleration data is collected and recording for each of the accelerometers 14 in the system 30 as described above. This data must be processed for meaningful analysis. Specifically, in accordance with the present invention, the actual linear and rotational acceleration of the head and the magnitude of the impact is estimated using the arrangement of single-axis accelerometers 14 in the system 30 as described above.

The data collected and recorded by the accelerometers is processed according to a novel algorithm of the present invention. The processing of the data with the novel algorithm of the present invention assumes that: 1) the accelerometers 14 are placed at known locations around the surface of the skull 16 of the head 12, as shown in FIG. 2; and 2) the surface of the skull 16 of the head 12 can be described geometrically.

Figure 3:
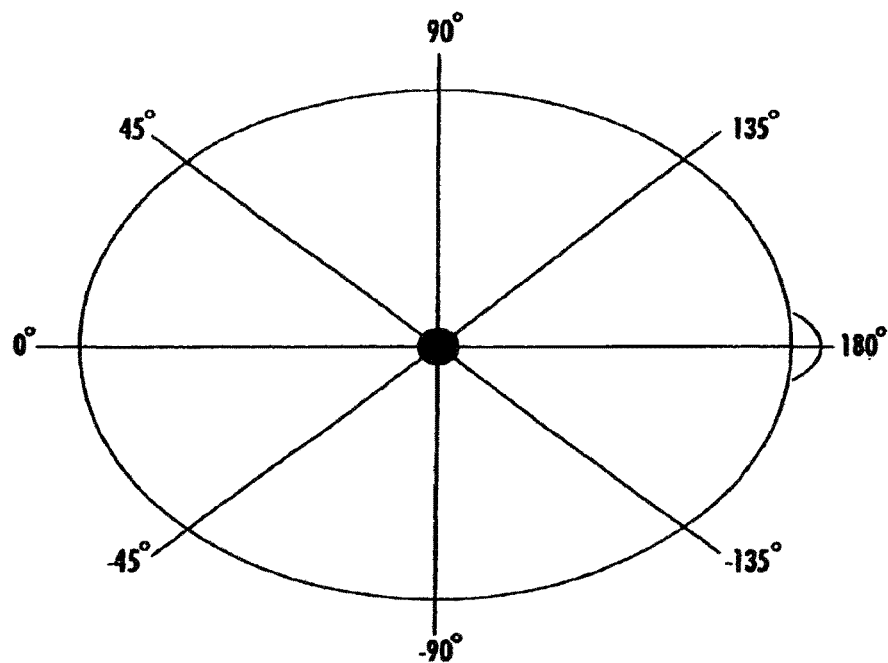
FIG. 3 is a schematic top view of a head with a coordinate system shown thereon.

For example, the novel algorithm can be demonstrated for a typical case where, in addition to the above assumptions, the following conditions are met: 1) the accelerometers 14 are placed at known locations around the transverse plane of the skull 16 of the head 12 passing through a point 18 located approximate to the center of gravity, as shown in FIG. 2; 2) the head cross-section (HCS) in this transverse plane is circular, and defines a radial coordinate system, as shown in FIG. 3; and 3) the impact is linear and lies within the transverse plane.

For these conditions, it can be shown that the magnitude of the linear acceleration normal to the HCS varies as the cosine of the arc (s) along the HCS. A Hit Profile is defined by the following function:

$$a*\cos(s-b)+c \tag{1}$$

where a=peak linear head acceleration (g's), s=arc (deg), b=hit location on the head (deg) and c=the offset. For a given impact and a specific configuration of accelerometers 14, i.e. the number and location of accelerometers 14, there will be a set of n acceleration profiles and peak accelerations. Given the location of each accelerometer, in degrees, in the HCS, a least-squares fit of the acceleration data to the Hit Profile yields the predicted peak linear head acceleration, a, and the predicted hit location, b, in the HCS. In the case where the impact is directed to the center of gravity of the head 12, the offset will be zero. Otherwise, as will be described below, axial rotational head acceleration will result requiring an offset value.

In general, the acceleration data is collected and recorded. A hit profile function is determined from the configuration of the body part and the positioning of the plurality of accelerometers thereabout. A number of potential hit results are generated from the hit profile function and then compared to the acceleration data sensed by the accelerometers. One of the potential hit results is best fit matched to the acceleration data to determine a best fit hit result. The magnitude and direction of an impact to the body part is determined from applying the hit profile function to the best fit hit result. The rotational acceleration of the body part can also be determined from the magnitude and direction of the impact to the body part and the offset.

Example of Application of Algorithm

Figure 8:
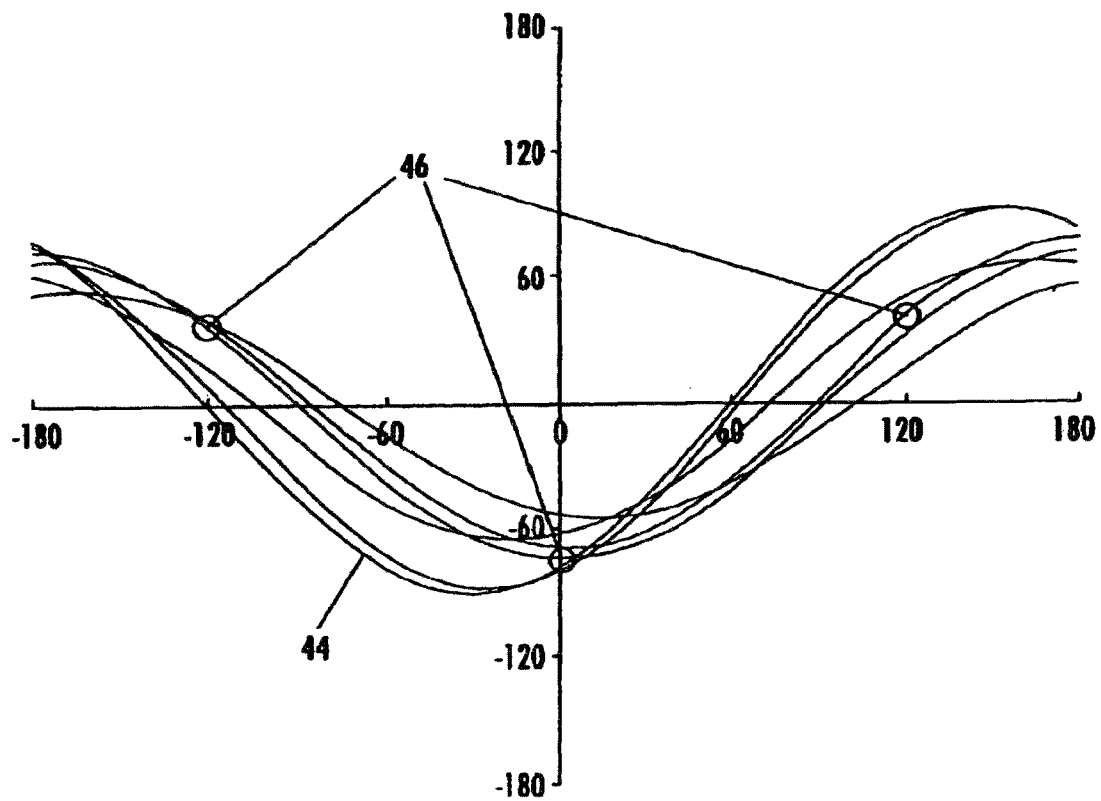
FIG. 8 is a graphical display of the fitting of the algorithm to the collected data.

As shown in FIG. 8, the acceleration data for a given array of three accelerometers is graphically displayed in two dimensions. In this example, the accelerometers are placed at the known locations of (−)120 degrees, 0 degrees and 120 degrees about the assumed circular circumference of the skull of a head with a known arc length s which is the radius r in FIG. 2. In this example, the accelerometers revealed an impact by sensing the following accelerations:

TABLE 1

| Location of Accelerometer in Coordinate System | Peak Acceleration Sensed (g) |
|---|---|
| (−) 120 | 75 |
| 0 | 8 |
| 120 | 75 |

These known parameters of the location of the accelerometers are used to create series of cosine waves from the above algorithm function which are each slightly different than one another. This series of waveforms correspond to the various potential hit magnitudes and hit locations calculated using Equation 1. These waveforms are considered potential hit results. As shown in FIG. 8, the series of waveforms 44 are mapped over the actual collected data 46. One of the waveforms 44 is selected as a best fit hit result by employing known least squares regression techniques. The non-selected waveforms are discarded. The selected best fit hit result, a cosine wave, is governed by the algorithm function above. Therefore, the additional variables of peak linear acceleration a and the hit location b in degrees can be determined by simply viewing the particular mathematical components of the selected best fit result. Thus, the magnitude of the linear acceleration and direction of impact can be calculated using only single-axis accelerometers.

The function above is employed when the HCS is assumed to be circular. Other functions are employed when the HCS is assumed to be other shapes, such as an ellipse. For an ellipse, the cosine wave hit profile is modified by multiplication of the tangent of the ellipse and by division of the tangent of a circle. Using a similar approach, the function for any geometric shape can be employed to generate the hit profile for a particular body part shape.

Further, rotational acceleration is also capable of being estimated from the linear data obtained from the single-axis accelerometers 14 and the estimation of the magnitude of acceleration and direction of impact. Specifically, In the case of impacts that are not directed towards the center of gravity, as shown in FIG. 2, an axial rotational acceleration is assumed to be induced about the z-axis, parallel to the spine through the neck or in the superior-inferior direction and through the center of gravity 18 of the head 12 The normal component of this rotational acceleration will be recorded by the linear accelerometers according to the following function:

$$a_n = r\omega^2 \quad (2)$$

where r is the distance from the z-axis passing through center of gravity of the head 12 to the accelerometers 14 and w is the angular velocity of the head 12. In this case, the algorithm for fitting the linear acceleration data to the cosine algorithm above works equivalently and accounts for the offset in linear acceleration data due to the normal component of angular acceleration. This offset defines axial rotational acceleration about the z-axis—and is one of the three components that completely describe the rotational acceleration of the skull. Thus, the rotational acceleration appears in the function in formula (I) above as the offset and can be easily determined from the selected best fit curve. The antero-posterior and medial-lateral bending acceleration of the skull are computed together by multiplying the estimated linear acceleration by the distance to the center of rotation of the neck for the given impact direction. This distance can be fixed for all impact directions, selected from a lookup table, or measured empirically. The estimate of the magnitude of the rotational acceleration of the skull is given as the magnitude of the axial, antero-posterior and medial-lateral bending acceleration of the skull.

Therefore, a further novel aspect of the system and method of the present invention is that computation of rotational acceleration is based on the impact location. Such a computation is made even without the assumption of orthogonality of the accelerometers relative to each other and computation of the impact vector using the fitting algorithm described above to collected data all using only single-axis accelerometers orthogonal to the surface of a body part.

The algorithm set forth above in formula (I) has been validated by comparison to theoretical and experimental data. The known inputs were: 1) number of accelerometers; 2) location on the transverse plane of the head of each accelerometer (measured in degrees), and, 3) magnitude (g's) and location (degrees) of the impact in the HCS. To validate the algorithm, a sensitivity analysis of the independent variables was performed. For a given set of these input variables, the correct (ideal) accelerations were calculated. To simulate variability that would be expected in practical applications of system 30, random noise was added to the location of the accelerometers 14 and to the acceleration values. The algorithm used this noisy data set (repeated 10 times for each parametric set of input variables) to predict the magnitude and location of the simulated hit. These values were then compared to the input (ideal) values. Parametric analyses were performed by changing the number of accelerometers 14, the location of each accelerometer 14 location, the standard deviation of the noise in the location of the accelerometers, and the standard deviation of the noise in the peak acceleration values of each accelerometer.

Sensitivity analyses showed that computed values for peak linear head acceleration and hit location were most sensitive to errors in accelerometer location compared to errors in acceleration magnitude. Table 2 below summarizes the effect on both estimated acceleration parameters and on commercial factors including cost and practical implementation.

TABLE 2

| Parameter | Effect on Decreasing Error in Estimated Peak Acceleration Compared to Actual | Effect on Decreasing Error in Estimated Impact Location Compared to Actual | Effect on System Cost | Effect on Practical Implementation of System in Helmets |
|---|---|---|---|---|
| Increased HMAS Measured Accuracy | ++ | ++ | + | + |
| Increased HMAS Location Accuracy | ++++ | ++++ | + | +++ |
| Increased Number of HMAS Units | +++ | +++ | +++ | ++++ |

Figure 9:
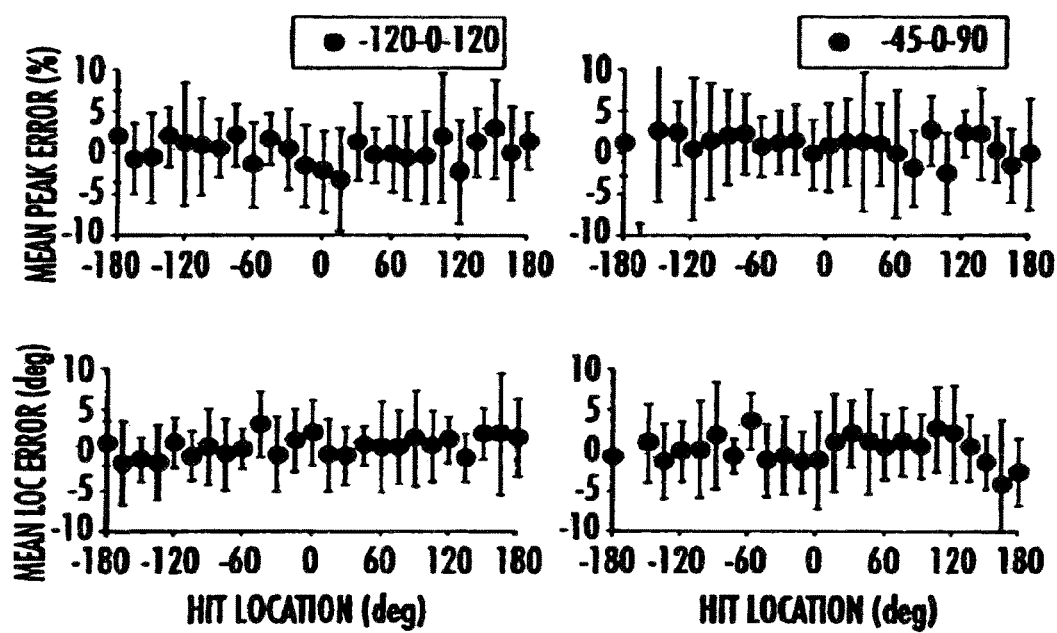
FIG. 9 is a graphical comparison of simulated peak acceleration and location of impact with ideal peak acceleration and location of impact for two sets of accelerometer orientations.

A configuration with 3 accelerometers spaced equally around the coordinate system of FIG. 3 at 120° was sufficient, as shown in FIG. 9, to achieve errors in acceleration magnitude of less than 10%. From a practical perspective, a 3 accelerometer system, with positions at 0°, 120°, -120° (0° was chosen as rear of the head, negative as left side and positive as right side from a rear view of the head as in FIG. 3), demonstrated minimum error in peak acceleration predicted with noisy acceleration data compared to the actual (ideal) input peak acceleration and impact location across all impact locations on the transverse plane. Maximum error was less than 10%. Accuracy did not begin to fall off substantially until the 3 accelerometers were within 30 degrees of one another. There was also only slight decrease in accuracy for asymmetrical accelerometer placements, such as 0°, 90°, −45°, which may be a more practical position for the units to be placed in the helmet. For brevity, the full parametric analysis is not reported.

Increasing from three accelerometers to six accelerometers resulted in a negligible increase in the accuracy of the estimated peak acceleration and estimated impact location for a given accelerometer configuration.

Increasing the number of accelerometers decreased error in estimated peak acceleration and impact location error for 30 g impact simulations (n=10) when the system variables accelerometer acceleration and accelerometer location were perturbed with random noise of 5% and 5 degrees, respectively.

For any single simulation at any hit location, the error did not exceed 10% or 10 degrees. It is concluded that as long as the accelerometer is accurate to within 5% and its location is known within 5 degrees, there is no substantial benefit to increasing the number of accelerometers from three to six. The three accelerometer configuration is preferred from a cost and data management perspective, and meets the desired specifications.

Laboratory testing with a three accelerometer configuration demonstrated that linear accelerations computed from the measured accelerometer accelerations were within 10% for impacts in the transverse plane when compared to an accelerometer at the center of gravity of the headform. Impact location was computed to be within 10.degree. of the actual value. Estimates of rotational accelerations using linear accelerometers were within 10% of computed values using video and direct measurement techniques.

A standard twin-wire drop system (ASTM F1446) was utilized for linear acceleration testing with a triaxial accelerometer mounted at the center of gravity of a standard ISO headform. Peak acceleration from each of the three accelerometers was used as input for estimating the linear acceleration using the least squares fit algorithm described above.

Actual accelerometer locations were measured using a laser protractor system. Five impacts at an impact velocity of approximately 2.2 m/s were recorded at 45° intervals around the transverse plane of the headform. Computed peak acceleration data were compared with linear accelerations measured by a triaxial accelerometer located at the center of gravity of the headform.

A separate guided drop tower (not shown) with free 2D rotation was utilized to compare measured linear and rotational accelerations from both accelerometers and triaxial accelerometer at the center of gravity of the headform with 2D rotational acceleration measured using a magnetohydrodynamic rotational velocity sensor, such as the ARS-01 from Phoenix, Ariz., and computed from a 2D high speed digital video system, such as Redlakes MotionScope (2000 Hz). Accelerations measured by the accelerometers and by the triaxial accelerometer are a combination of linear acceleration and the normal component of the rotational acceleration.

The normal component: $a_n = r\omega^2$, can then be solved for $\omega$, and differentiated to determine the rotational acceleration. Alternatively, the tangential component: at $a_t = r\alpha$, can be solved directly for $\alpha$, the rotational acceleration. We assume that the head and neck acts as a rigid body during the impact. The radius, r, was the distance from the pivot point on the experimental apparatus and the center of gravity of the headform. Error analysis was performed by comparing 2D rotational accelerations estimated from our system with the calculated rotational accelerations from the high-speed video and the ARS sensor. For example, for a 2.2 m/sec drop, rotational accelerations on the order of 2000 rad/sec$^2$ were measured from the video, and compared with an estimated 1900 rad/sec$^2$ from the linear accelerometers, representing approximately 5% difference.

Thus, the algorithm in accordance with the present invention was validated by demonstrating that the error in estimated peak acceleration and estimated impact location was within ±10% of actual (ideal) when the system variables accelerometer acceleration and accelerometer location were perturbed with random noise of 5% and 5 degrees, respectively. The standard error bars, shown in FIG. 9, illustrate variability with 10 simulations.

Estimates of linear and rotational acceleration from experimental data collected with the system 30 were within ±10% of peak acceleration compared to acceleration measurements taken at the center of gravity of the test headform. Reproducibility of the system was within ±5%.

As shown above, the algorithm for estimating linear and rotational acceleration and magnitude has been validated for 2D and for impacts along the transverse plane. In accordance with the present invention, the algorithm can be readily modified to 3D and tested both theoretically and experimentally.

Therefore, the present invention provides for single axis accelerometers to be incorporated into an helmet such that the accelerometer is in apposition to the surface of the head and can worn by a user. Dual and tri-axis accelerometers may also be used to collect and record additional information, such as acceleration tangent to the surface of the skull, for further analysis and study.

The system 30 of the present invention enables the relationship between biomechanical measures of linear and rotational acceleration and the clinically determined incidence of MTBI across demographic groups to be quantified, with a particular emphasis on children and youth in sports. The system 30 is capable of automatic monitoring of impact incidence and will provide a basis for testing hypotheses relating impact severity and history to MTBI.

While the specific embodiments have been illustrated and described, numerous modifications come to mind without significantly departing from the spirit of the invention, and the scope of protection is only limited by the scope of the accompanying Claims.

What is claimed is:

1. A real-time impact monitoring system for use with multiple players engaged in a sporting activity, each player wearing a protective helmet, the system comprising:
 a first helmet worn by a first player, said helmet having an external shell, an internal padding assembly and an interface liner removably positioned within the internal padding assembly, the interface liner configured to be in contact with the first player's head while the helmet is worn, the interface liner including a sensing and control unit having a plurality of sensors arrayed within the interface liner that detect helmet impact data, a processor that compares the helmet impact data against pre-loaded impact profiles, and a transmitter to transmit impact data;
 a second helmet worn by a second player, said helmet having an external shell, an internal padding assembly and an interface liner removably positioned within the internal padding assembly, the interface liner configured to be in contact with the second player's head while the helmet is worn, the interface liner including a sensing and control unit having a plurality of sensors arrayed within the interface liner that detect helmet impact data, a processor that compares the helmet impact data against pre-loaded impact profiles, and a transmitter to transmit impact data; and, a remote unit operably connected to the plurality of sensing and control units, the remote unit having a receiver configured to receive the impact data transmitted from the each of the first and second sensing and control units.

2. The real-time impact monitoring system of claim 1, wherein each sensing and control unit includes at least one filter that provides signal conditioning for the impact data.

3. The real-time impact monitoring system of claim 1, wherein each sensing and control unit includes at least one battery.

4. The real-time impact monitoring system of claim 1, wherein the processor further determines the direction of the impacts to the helmets.

5. The real-time impact monitoring system of claim 1, wherein the interface liner has a flexible multi-layer construction with at least one padding element within an outer liner housing.

6. The real-time impact monitoring system of claim 1, wherein the interface liner has a multi-layer configuration that allows the interface liner to match the configuration of the player's head, whereby the interface liner resides between the player's head and the internal padding assembly.

7. The real-time impact monitoring system of claim 1, the system further comprises a graphical user interface operably connected to the remote unit for immediately displaying at least one of the magnitude of impacts to the plurality of helmets.

8. A real-time impact monitoring system for protective sports equipment worn by a player engaged in a sporting activity, the impact monitoring system comprising:

a protective body part assembly including a protective outer layer and a padding assembly that is configured to reside inward of the protective outer layer and against the player's body part during the sporting activity;

an interface liner removably positioned within the padding assembly of the protective body part assembly, the interface liner configured to also reside against the player's body part while the protective body part assembly is worn, the interface liner including a sensing and control unit having a plurality of sensors arrayed within the interface liner that detect impact data resulting from impacts to the protective body part assembly, the interface liner further including a processor that compares the impact data against pre-loaded impact profiles, and a transmitter to transmit impact data; and, a remote unit operably connected to the sensing and control unit, the remote unit having a receiver configured to receive the impact data transmitted from the sensing and control unit.

9. The impact monitoring system of claim 8, wherein the sensing and control unit includes at least one filter that provides signal conditioning for the impact data.

10. The impact monitoring system of claim 8, wherein the processor further determines the direction of the impacts to the protective body part assembly.

11. The impact monitoring system of claim 8, wherein the interface liner has a flexible multi-layer construction with at least one padding element within an outer liner housing.

12. The impact monitoring system of claim 8, the system further comprises a graphical user interface operably connected to the remote unit for immediately displaying at least one of the magnitude of impacts to the protective body part assembly.

13. The real-time impact monitoring system of claim 1, wherein the plurality of sensors are arrayed within the interface liner about the periphery of the player's head while the helmet is worn.

14. The real-time impact monitoring system of claim 13, wherein the sensors are configured to sense the linear and rotational acceleration of the player's head resulting from an impact to the helmet.

15. The real-time impact monitoring system of claim 13, wherein the sensors are accelerometers configured to sense the linear and rotational acceleration of the player's head resulting from an impact to the helmet.

16. The real-time impact monitoring system of claim 15, wherein the sensors are tri-axial accelerometers.

17. The real-time impact monitoring system of claim 8, wherein the plurality of sensors are arrayed within the interface liner about the periphery of the player's body part while the protective body part assembly is worn.

18. The real-time impact monitoring system of claim 17, wherein the sensors are configured to sense the linear and rotational acceleration of the player's body part resulting from an impact to the helmet.

19. The real-time impact monitoring system of claim 17, wherein the sensors are accelerometers configured to sense the linear and rotational acceleration of the player's body part resulting from an impact to the helmet.

20. The real-time impact monitoring system of claim 17, wherein the sensors are tri-axial accelerometers.

* * * * *